US009295841B2

(12) United States Patent
Fang et al.

(10) Patent No.: US 9,295,841 B2
(45) Date of Patent: *Mar. 29, 2016

(54) HIGH-FREQUENCY ELECTRICAL NERVE BLOCK

(71) Applicants: Zi-Ping Fang, Beachwood, OH (US); Jon J. Snyder, Kirtland, OH (US); Nemath Syed Shah, Lyndhurst, OH (US)

(72) Inventors: Zi-Ping Fang, Beachwood, OH (US); Jon J. Snyder, Kirtland, OH (US); Nemath Syed Shah, Lyndhurst, OH (US)

(73) Assignee: Meuros Medical, Inc., Willoughby Hills, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/656,256

(22) Filed: Mar. 12, 2015

(65) Prior Publication Data
US 2015/0182749 A1 Jul. 2, 2015

Related U.S. Application Data

(63) Continuation-in-part of application No. 14/276,200, filed on May 13, 2014, now Pat. No. 8,983,612, which is a continuation of application No. 13/474,926, filed on May 18, 2012, now Pat. No. 8,731,676.

(60) Provisional application No. 61/487,877, filed on May 19, 2011.

(51) Int. Cl.
*A61N 1/36* (2006.01)
*A61N 1/05* (2006.01)

(52) U.S. Cl.
CPC .......... *A61N 1/36071* (2013.01); *A61N 1/0551* (2013.01); *A61N 1/0556* (2013.01); *A61N 1/36153* (2013.01); *A61N 1/36157* (2013.01); *A61N 1/36171* (2013.01)

(58) Field of Classification Search
CPC ....... A61N 1/05; A61N 1/056; A61N 1/0551; A61N 1/36021; A61N 1/36071; A61N 1/3605
USPC .......................................... 607/47, 116, 117
See application file for complete search history.

(56) References Cited

U.S. PATENT DOCUMENTS

| | | | |
|---|---|---|---|
| 3,738,368 A * | 6/1973 | Avery et al. | 607/117 |
| 4,155,366 A * | 5/1979 | Di Mucci | 607/46 |
| 4,573,481 A | 3/1986 | Bullara | |
| 4,602,624 A | 7/1986 | Naples et al. | |
| 4,979,511 A | 12/1990 | Terry, Jr. | |
| 5,755,750 A | 5/1998 | Petruska et al. | |
| 6,456,866 B1 | 9/2002 | Tyler et al. | |

(Continued)

FOREIGN PATENT DOCUMENTS

WO 2009/058258 5/2009

OTHER PUBLICATIONS

Ackermann et al. Effect of bipolar cuff electrode design on block thresholds in high-frequency electrical neural conduction block. IEEE Transactions on Neural Systems and Rehabilitation. (2009): 469-77.

(Continued)

*Primary Examiner* — Christopher D Koharski
*Assistant Examiner* — Roland Dinga
(74) *Attorney, Agent, or Firm* — Thompson Hine LLP

(57) ABSTRACT

A method and apparatus that resulted in blocking an action potential in a nerve.

15 Claims, 17 Drawing Sheets

(56) References Cited

U.S. PATENT DOCUMENTS

| | | | |
|---|---|---|---|
| 6,699,275 | B1 | 3/2004 | Knudson et al. |
| 6,836,685 | B1 | 12/2004 | Fitz |
| 6,860,851 | B2 | 3/2005 | Knudson et al. |
| 7,167,750 | B2 | 1/2007 | Knudson et al. |
| 7,201,757 | B2 | 4/2007 | Knudson et al. |
| 7,292,890 | B2 | 11/2007 | Whitehurst et al. |
| 7,389,145 | B2 | 6/2008 | Kilgore et al. |
| 7,444,183 | B2 | 10/2008 | Knudson et al. |
| 7,783,362 | B2 | 8/2010 | Whitehurst et al. |
| 7,860,570 | B2 | 12/2010 | Whitehurst et al. |
| 8,060,208 | B2 | 11/2011 | Kilgore et al. |
| 8,108,052 | B2 | 1/2012 | Boling |
| 8,170,675 | B2 | 5/2012 | Alataris et al. |
| 2002/0055779 | A1 | 5/2002 | Andrews |
| 2002/0198572 | A1 | 12/2002 | Weiner |
| 2003/0144709 | A1 | 7/2003 | Zabara et al. |
| 2004/0243182 | A1 | 12/2004 | Cohen et al. |
| 2005/0131485 | A1 | 6/2005 | Knudson et al. |
| 2005/0143789 | A1 | 6/2005 | Whitehurst et al. |
| 2005/0149154 | A1 | 7/2005 | Cohen et al. |
| 2006/0195158 | A1 | 8/2006 | Cory |
| 2006/0271137 | A1* | 11/2006 | Stanton-Hicks ............... 607/118 |
| 2006/0293721 | A1 | 12/2006 | Tarver et al. |
| 2008/0046055 | A1 | 2/2008 | Durand et al. |
| 2008/0086180 | A1 | 4/2008 | Ben-Ezra et al. |
| 2008/0183226 | A1 | 7/2008 | Buras et al. |
| 2008/0294221 | A1 | 11/2008 | Kilgore et al. |
| 2009/0204173 | A1 | 8/2009 | Fang et al. |
| 2010/0211135 | A1 | 8/2010 | Caparso et al. |
| 2010/0241190 | A1* | 9/2010 | Kilgore et al. .................. 607/48 |
| 2010/0274312 | A1 | 10/2010 | Alataris et al. |
| 2010/0274314 | A1 | 10/2010 | Alataris et al. |
| 2010/0274315 | A1 | 10/2010 | Alataris et al. |
| 2010/0274316 | A1 | 10/2010 | Alataris et al. |
| 2010/0274317 | A1 | 10/2010 | Parker et al. |
| 2010/0274318 | A1 | 10/2010 | Walker et al. |
| 2010/0274326 | A1 | 10/2010 | Chitre et al. |
| 2011/0071593 | A1 | 3/2011 | Parker et al. |
| 2011/0077721 | A1 | 3/2011 | Whitehurst et al. |
| 2011/0230701 | A1 | 9/2011 | Simon et al. |
| 2012/0016439 | A1 | 1/2012 | Alataris et al. |
| 2012/0083709 | A1 | 4/2012 | Parker et al. |

OTHER PUBLICATIONS

Ackermann et al. Electrical conduction block in large nerves: high frequency current delivery in the nonhuman primate. Muscle Nerve. 43 (2011) 897-899.
Becker and Reed. Essentials of local anesthetic pharmacology. Anesth Prog 53 (2006) 98-109.
Bhadra and Kilgore. High-frequency electrical conduction block of mammalian peripheral motor nerve. Muscle & Nerve. (2005) 782-790.
Bhadra et al. Simulation of high-frequency sinusoidal electrical block of mammalian myelinated axons. J Comput Neurosci 22 (2007) 313-326.
Cleeland and Ryan. Pain assessment: global use of the brief pain inventory. 23 (1994 129-138.
Dickinson et al. Maldynia: pathophysiology and management of neuropathic and maladaptive pain—a report of the ama council on science and public healthpme. Pain Medicine 11 (2010) 1635-1653.
Dworkin et al. Interpreting the clinical importance of treatment outcomes in chronic pain clinical trials: IMMPACT recommendations. The Journal of Pain 9 (2008) 105-121.
Fisher et al. Chronic stability and selectivity of four-contact spiral nerve-cuff electrodes in stimulating the human femoral nerve. J. Neural Eng. 6 (2009) 1-9.
Flor et al. Phantom limb pain: a case of maladaptive CNS plasticity? Neuroscience 7 (2006) 873-881.
Fyfe. An audit of amputation levels in patients referred for prosthetic rehabilitation. Prosthetics and Orthotics International 14 (1990), 67-70.
Gerges et al. Frequency and amplitude transitioned waveforms mitigate the onset response in high frequency nerve block. J Neural Eng. 7 (2010) 1-17.
Guse and Moran. Outcomes of the surgical treatment of peripheral neuromas of the hand and forearm. Hand Surgery 00 (2012) 1-5.
Haroutounian et al. Primary afferent input critical for maintaining spontaneous pain in peripheral neuropathy. PAIN 155 (2014) 1272-1279.
Hsu and Cohen. Postamputation pain: epidemiology, mechanisms, and treatment. Journal of Pain Research. (2013) 121-136.
Keller et al. Validity of the brief pain inventory for use in documenting the outcomes of patients with noncancer pain. Clin J. Pain 20 (2004) 309-317.
Kilgore and Bhadra. Nerve conduction block utilizing high-frequency alternating current. Med. Biol. Eng. Comput. 42 (2004) 394-406.
Kilgore and Bhadra. Reversible nerve conduction block using kilohertz frequency alternating current. Neuromodulation 17 (2014) 242-255.
Kumar et al. Spinal cord stimulation versus conventional medical management for neuropathic pain: A multicentre randomised controlled trial in patients with failed back surgery syndrome. Pain 132 (2007) 179-188.
Leland and Oboroceanu. American war and military operations casualties: lists and statistics. Congressional Research Service (210) 1-30.
Lewin-Kowalik et al. Phantom limb pain: mechanisms and treatment approaches. Neurol Med Chir (Tokyo) 46 (2006) 62-68.
Melzack and Wall. Pain mechanisms: a new theory. Science 150 (1965) 971-979.
Naples et al. A spiral nerve cuff electrode for peripheral nerve stimulation. IEEE Transactions on Biomedical Engineering 35 (1988) 905-916.
Narang et al. Functional capabilities of lower limb amputees. Prosthetics and Orthotics International 8 (1984) 43-51.
NLLIC Staff. Fact Sheet. Amputation Statistics by Cause Limb Loss in the United States. Amputee Coalition of America (2008) 1-3.
North et al. Spinal cord stimulation versus re-operation in patients with failed back surgery syndrome: an international multicenter randomized controlled trial (Evidence study). Neuromodulation 14 (2011) 330-336.
Polasek et al. Stimulation stability and selectivity of chronically implanted multicontact nerve cuff electrodes in the human upper extremity. IEEE Transactions on Neural Systems and Rehabilitation Engineering, 17 (2009) 428-437.
Saper et al. Occipital nerve stimulation for the treatment of intractable chronic migraine headache: ONSTIM feasibility study. Cephalalgia 31 (2010) 271-285.
Schoppen et al. Physical, mental, and social predictors of functional outcome in unilateral lower-limb amputees. Arch Phys Med Rehabil 84 (2003) 803-811.
Soin et al. Abstract. Feasibility study on high-frequency electrical nerve block for amputation pain. International Neuromodulation Society 2011 561.
Soin et al. 1730-1740 Peripheral Nerve Jun. 11, 2010. Pilot study on high-frequency nerve block for amputation pain: initial results. International Neuromodulation Society Jun. 11, 2013 p. e98.
Subedi and Grossberg. Phantom limb pain:mechanisms and treatment approaches. Pain Research and Treatment. 2011 1-8.
Vaso et al. Peripheral nervous system origin of phantom limb pain. PAIN 155 (2014) 1384-1391.
Waataja et al. Effects of high-frequency alternating current on axonal conduction through the vagus nerve. J. Neural Eng. 8 (2011) 1-7.
Ziegler et al. Estimating the Prevalence of Limb Loss in the United States: 2005 to 2050. Arch Phys Med Rehabil 89 (2008) 422-429.
Page et al. Oral Posters—Intrathechecal Drug Delivery for Pain and Spasticity: 2013 1630-1640 Spine Jun. 11, 2004. Effect of intratecal intermittent boluses and morphine concerntration on the incidence of inflammatory mass in a canine model. International Modulation Society Jun. 11, 2013 e94¶.

* cited by examiner

FIG 8: Summary of Feasibility Study Results
Electrical Nerve Block for Amputation Pain

| Subject | 1 | 2 | 3 | 4 | 5 |
|---|---|---|---|---|---|
| Gender, age | Male, 37 | Male, 54 | Female, 53 | Male, 76 | Male, 52 |
| Cause of amputation | Dysvascular | Dysvascular | Infection | Trauma | Trauma |
| Level of Amputation | Below knee | Above knee | Above knee | Below knee | Above knee |
| Nerve blocked | Tibial | Sciatic | Sciatic | Tibial | Sciatic |
| Spontaneous pain intensity at each visit | 3, 3, 3 | 0, 0, 0, 0 | 0, 0 | 8, 8, 7, 7 | 0, 7, 7 |
| Induced pain intensity by pressing the neuroma | Not tried | 9 | 7 | 5 | 8 |
| In-clinic test result: number of sessions with significant/partial/no pain reductions | 1/2/5 | 3/1/2 | 0/3/1 | 6/1/0 | 7/0/0 |
| At-home use result: number of sessions with significant/partial/no pain reductions | 0/0/1 | Not used | Not used | 13/0/0 | 4/0/0 |
| Conclusion | Success in clinic | Success in clinic | Not successful | Complete success | Complete success |

FIG. 9

| Subject No. | 1 | 2 | 3 | 4 | 5 | 6 | 7 | 8 | 9 | 10 |
|---|---|---|---|---|---|---|---|---|---|---|
| Gender | Male | Female | Male | Female | Female | Female | Female | Male | Female | Male |
| Age | 77 | 49 | 53 | 55 | 59 | 57 | 55 | 43 | 60 | 27 |
| Cause of amputation | Trauma | Vascular | Trauma | Infection | Vascular | Trauma | Trauma | Vascular | Vascular | Trauma |
| Level of amputation (from knee) | Below | Below | Above | Above | Below | Below | Below | Below | Above | Above |
| Time since amputation | 7 years | 1 year | 8 years | 18 years | 4 years | 10 years | 2 years | 0.8 years | 6 years | 11 years |
| Prosthetic leg | Yes | No | No | No | No | Yes | Yes | Yes | No | Yes |
| Pain location | Stump | Stump | Phantom | Stump | Stump | Stump | Stump | Stump | Phantom | Phantom |
| Pain intensity worst, usual, least | 8, 4, 3 | 10, 9, 7 | 10, 6, 3 | 10, 4, 2 | 10, 8, 0 | 10, 6, 6 | 10, 8, 2 | 9, 5, 0 | 10, 6, 4 | 10, 5, 5 |
| Pain type | Persistent | Persistent | Persistent | Episodic | Persistent | Persistent | Persistent | Persistent | Episodic | Persistent |
| Pain frequency | 5-7/day | 5-7/day | 5/day | 2/week | 5/week | 7/week | 2/day | 3/day | ≥2/week | 5-6/week |
| Analgesics used | None | Opioids | NSAIDs/ Opioids | Opioids | NSAIDs | Opioids | Opioids | Opioids | Opioids | Opioids |
| Pain-reduction by lidocaine (twice) | 60%, 80% | 50%, 50% | 100%, 50% | 90%, 60% | 50%, 100% | 50%, 50% | 100%, 80% | 100%, 60% | 100%, 100% | 70%, 60% |

FIG. 10

| Subject | Nerve | Nerve Diameter (mm) | Frequency (kHz) | Electrode Impedance (Ω) | Ramp-up Duration (min) | Plateau Duration (min) | External Generator Initial Voltage (V) | External Generator Plateau Voltage (V) | Implanted generator Initial Voltage (V) | Implanted generator Plateau Voltage (V) |
|---|---|---|---|---|---|---|---|---|---|---|
| 1 | Tibial | 8 | 10 | 556 | 5 | 25 | 1.0 | 2.0 | 0.0 | 3.0 |
| 3 | Sciatic | 12 | 5 | 452 | 5 | 25 | 0.0 | 5.5 | 0.0 | 7.0 |
| 4 | Sciatic | 10 | 10 | 676 | 5 | 25 | 0.0 | 7.0 | 0.0 | 7.0 |
| 5 | Sciatic | 8 | 10 | 500 | 10 | 20 | 1.0 | 2.3 | - | - |
| 7 | Tibial | 6 | 10 | 748 | 5 | 25 | 1.0 | 2.7 | 1.0 | 2.0 |
| 9 | Sciatic | 10 | 10 | 558 | 5 | 25 | 0.5 | 3.5 | 0.0 | 4.0 |
| 10 | Sciatic | 12 | 10 | 852 | 5 | 25 | 3.0 | 6.0 | 2.5 | 10.0 |

FIG. 11A
FIG. 11B
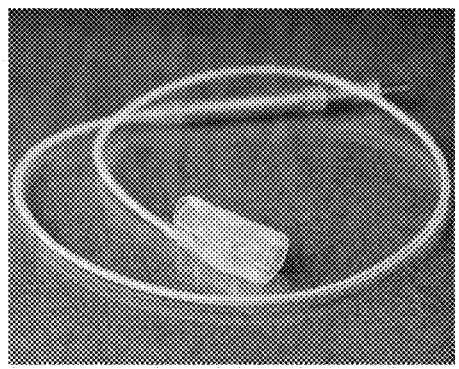
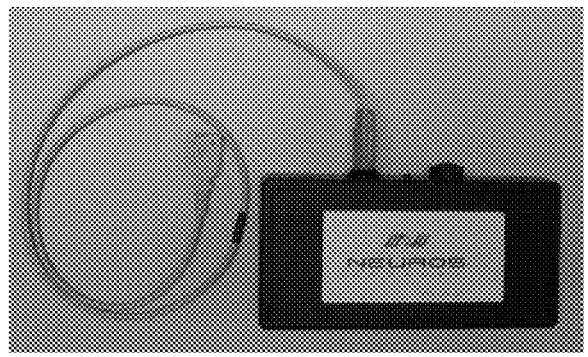
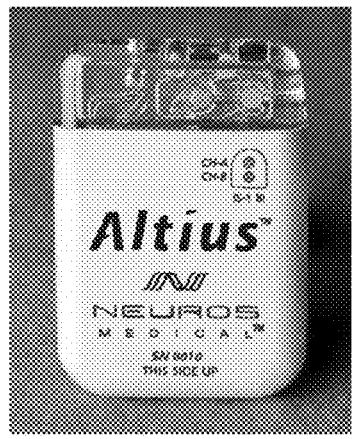
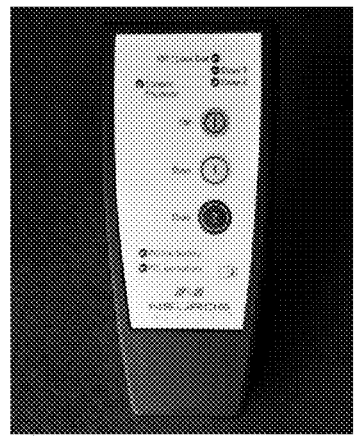
FIG. 11C
FIG. 11D

Group average

Group average

HIGH-FREQUENCY ELECTRICAL NERVE BLOCK

This application is a continuation-in-part of co-pending U.S. application Ser. No. 14/276,200 filed May 13, 2014; which is a continuation of Ser. No. 13/474,926 filed May 18, 2012 now U.S. Pat. No. 8,731,676; which claims priority to U.S. application Ser. No. 61/487,877 filed May 19, 2011, each of which is expressly incorporated by reference herein in its entirety.

In one embodiment, successful results are disclosed from a method and apparatus that uses high frequency nerve block to acutely treat peripheral pain, either acute pain or chronic pain (more than 6 months in duration), in humans by blocking nerve conduction of an action potential. Acute treatment is defined as on demand treatment with substantially immediate pain relief effect. In one embodiment, the method is used in peripheral nerves having a diameter up to about 12 mm, i.e., in relatively large nerves such as the sciatic nerve. In one embodiment, the method is used on a nerve to ameliorate a non-pain condition by therapy to a nerve, e.g., motor nerves resulting in spasticity, e.g., nerves providing an urge to void in overactive bladder.

Previous therapy for pain of peripheral origin, e.g., damaged nerves in a limb, consisted of one or a combination of the following methods.

One previous therapy was local injection of a pharmacologic anesthetic such as lidocaine. The therapeutic effect often lasts only a short time, e.g., a few hours. Repeated dosing is typically not feasible because of toxicity of the anesthetic and other reasons.

Another previous therapy was conventional electrical stimulation by surface electrodes or surgically implanted electrodes (e.g., TENS, Peripheral Nerve and Spinal Cord Stimulator). Electrical stimulation therapy is used to treat back pain and joint pain, but produces inconsistent effects. The inconsistencies are due to the indirect nature of the therapy; instead of blocking pain signals from the origin of the pain, this type of electrical stimulation activates non-pain sensory nerves to generate other types of sensation (e.g., tingling) that mask the pain sensation. Such masking is by a complex, and often unreliable, interaction of various parts of the nervous system.

A potential therapy involves reversibly blocking peripheral nerves by applying high frequency alternating current directly on a nerve trunk. Specifically, a current ranging from 5 kHz to 50 kHz was applied; this was denoted as high frequency, compared to a current of less than 1 kHz applied in the conventional electrical stimulation described above. Efficacy of the high frequency alternating current therapy in acute non-human animal experiments (frog, cat) has been reported. U.S. Pat. Nos. 7,389,145 and 8,060,208 describe in general this electrical stimulation technology. No data are described.

One embodiment of the invention discloses a method for reversibly blocking an action potential in a peripheral nerve having a diameter exceeding 3 mm and up to about 12 mm, e.g., a sciatic nerve, a tibial nerve, etc., in a patient in need thereof. The method comprises providing an electrical waveform for an interval of time sufficient to effect substantially immediate pain relief, defined generally as within about 10 min. One embodiment uses a waveform ranging from 5 kHz to 50 kHz. One embodiment uses a 10 kHz sinusoidal waveform at a current ranging from 4 mApp to 26 mApp. The electrode can be retained in a cuff encircling the desired peripheral nerve in which the action potential is to be blocked; the cuff inner diameter may range from about 5 mm to about 12 mm. The time interval may be about 10 minutes, but an interval may be selected by a magnitude sufficient to effect pain relief in the patient. In one embodiment, the electrical waveform to effect pain relief ranges from a voltage from 4 Vpp to 20 Vpp, or a current ranging from 4 mApp to 26 mApp. The time of increasing magnitude can range from about 10 seconds to about 60 seconds with a steady ramp up of voltage or current. The waveform is provided by a waveform generator that is operatively connected to the electrode implanted in the patient; such methods are known in the art.

One embodiment is a device that reversibly blocks an action potential in a relatively large nerve, i.e., a nerve with a diameter exceeding about 3 mm and up to 12 mm. The apparatus has a self-curling sheet of non-conductive material that includes a first layer, which is pre-tensioned, and a second layer, which is not pre-tensioned. The two layers are configured to form a cuff containing or holding strips of conducive material therebetween. In embodiments, the device has one, two, three, four or more continuous strips of a conductive material that are disposed adjacent, but not transverse, to one longitudinally extending edge of the self-curling sheet, each of these strips of conductive material is connected to an electrically conductive lead. In one embodiment, the device contains one strip of a conductive material, termed a monopolar configuration. In one embodiment, the device contains at least two continuous strips, connected by an electrically conductive lead, of a conductive material, termed a bipolar configuration. In one embodiment, the device contains at least three continuous strips, connected by an electrically conductive lead, of a conductive material, termed a tripolar configuration. In one embodiment, the device contains at least four continuous strips, connected by an electrically conductive lead, of a conductive material. Multiple apertures, typically circular but not necessarily so limited in shape, are disposed at periodic intervals of the inner nerve-contacting surface along the curling length of one of the two non-conductive sheets or layers of the self-curling sheet/cuff. This provides contact to the nerve by exposing and providing continuous multiple conductive contact points. The exposure may be at any interval that exposes as much of the conductive material as possible or desirable, and exceeds the contact surface area of conventional electrodes. Each of the first or top non-conductive sheet or layer and the second or bottom non-conductive sheet or layer still retains and contains the conductive material therebetween, i.e., sandwiched inside the sheets or layers, so that the conductive material is in fact retained and does not pop out or come out while providing efficient current delivery. In one embodiment the non-conductive material is silicon, the electrically conductive lead is stainless steel, and the conductive material is platinum. Other materials for each of the non-conductive material, the electrically conductive lead or wire, and the conductive material are known in the art. In use, the device is operatively connected, e.g., by an external lead or wire, to a waveform generator that provides the regulated waveform.

One embodiment is a method for treating peripheral nerve pain in a patient in need of this treatment. The above-described device encircled a particular segment of a targeted peripheral nerve, e.g., a sciatic nerve, a tibial nerve. Using a patient-implanted electrode connected to an electrical waveform generator, an electrical waveform is applied for a time interval, e.g., 10 min, sufficient to effect substantially immediate patient pain relief, e.g., within 10 min, and an extended period of pain relief up to several hours. The current in one embodiment ranges from 4 mApp to 26 mApp, and in one embodiment ranges from 4 mApp to 26 mApp.

In the inventive method, data from a human study using high frequency electrical nerve block technology for pain management are provided. In one embodiment, the result was that amputation pain was reduced. Application of 10 kHz alternating current generated by a custom generator via a custom implanted nerve electrode significantly reduced pain in the majority of patients treated by the method. The required voltage/current level is reported. The duration for achieving reliable pain relief in specific human nerves is reported. The required sequence and time to apply the electrical energy to minimize side effects is reported. The anticipated accompanying sensations and their time course is reported. The duration of pain relief after termination of the electrical current is reported. The cumulative effect of successive applications of the current on the extent of pain reduction is reported.

The apparatus was an implantable electrode operatively connected to an external or implanted waveform generator. The electrode was a spiral cuff electrode similar to that described in U.S. Pat. No. 4,602,624, more fully described below. In use, the electrode was implanted in a human mammal on a desired peripheral nerve trunk proximal to the pain source (e.g., a neuroma), such that the cuff encircled the desired peripheral nerve in which the action potential was to be blocked. The cuff inner diameter ranged from about 5 mm to about 12 mm. The sciatic nerve is known to have a relatively large nerve trunk; the diameter of the proximal part of the sciatic nerve in a human adult is about 12 mm. In one embodiment, the apparatus and method was used on the sciatic nerve to treat limb pain in above knee amputees. In one embodiment, the apparatus and method was used on the tibial nerve to treat limb pain in below knee amputees.

BRIEF DESCRIPTION OF THE DRAWINGS

FIG. 8 tabulates treatment outcomes from five patients.

FIG. 9 provides demographics, amputation, and pain characteristics of ten patients.

FIG. 10 provides therapy parameters for a group of seven patients.

FIGS. 11A, 11B, 11O, and 11D are photographs of a nerve cuff electrode, an external waveform generator, an implantable waveform generator, and a controller for an implantable generator, respectively.

Figure 1:
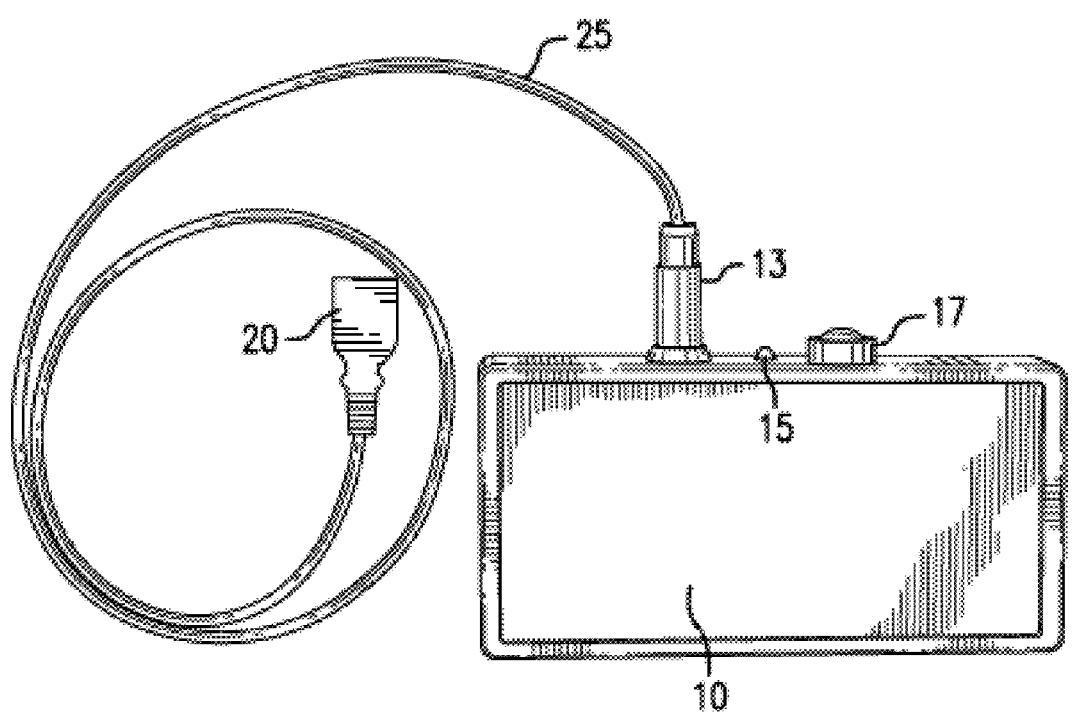
FIG. 1 is a perspective view of an external waveform generator and interconnection cable.
Figure 2:
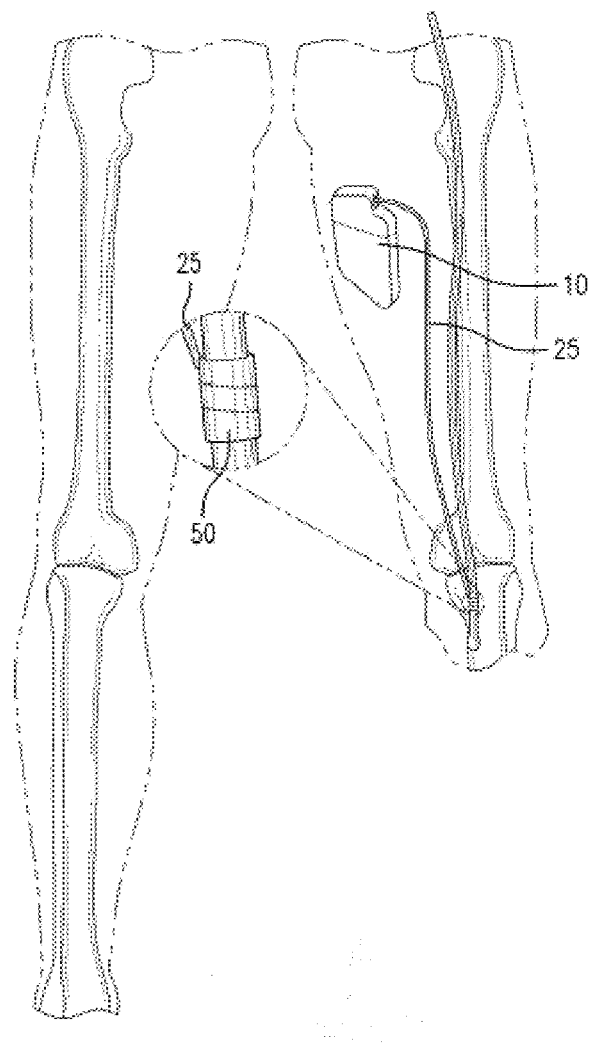
FIG. 2 shows an in-use implanted waveform generator operably connected to a nerve cuff electrode encircling a patient's nerve.

In use, the external and implanted waveform generator, shown in FIGS. 1 and 2 respectively, delivered high frequency alternating current in any form (sinusoidal wave, rectangular, other shape) sufficient to block the nerve action potential. In use, the operator selectively regulated the amount of current applied to the electrode, the duration, and any other desired parameters (e.g., continuous versus intermittent), etc. for therapy. In one embodiment, a sinusoidal waveform frequency of 10 kHz effectively and repeatedly reduced pain. In one embodiment, a sinusoidal waveform frequency ranging from 20 kHz to 30 kHz effectively reduced pain, but required about two times higher voltage and higher current for a 20 kHz sinusoidal waveform, and about three times higher voltage and higher current for a 30 kHz sinusoidal waveform, compared to that required for a 10 kHz sinusoidal waveform.

Using a sinusoidal waveform frequency of 10 kHz, patients reported a sensation threshold at a voltage ranging from 1 Vpp to 10 Vpp, and at a current ranging from 1 mApp to 16 mApp. The sensation threshold was the minimum stimulation at which a patient indicated that s/he feels a sensation due to the applied current, e.g., a patient may feel a tingling sensation.

Indication of a sensation threshold does not indicate pain relief, which is defined broadly as any pain mitigation or amelioration including but not limited to complete pain relief. Using a sinusoidal waveform of 10 kHz, the patient's relief from pain was achieved at a voltage ranging from 4 Vpp to 20 Vpp, and at a current ranging from 4 mApp to 26 mApp. The interval between the two parameters (the voltage/current required to be applied to achieve a sensation threshold, versus the voltage/current required to be applied to achieve pain relief) was optimally achieved by a conservative steady ramping up over a range from about 10 seconds to about 60 seconds. This minimized or prevented the patient from experiencing pain or other undesirable sensations at the outset of therapy.

Figure 3A:
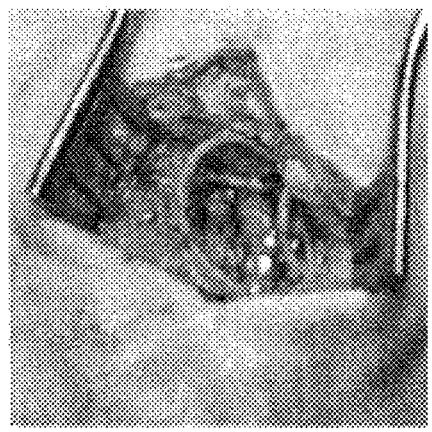
FIGS. 3A, 3B are a photograph on the implanted cuff and electrode, and a confirmatory fluoroscopy image of same, respectively.
Figure 3B:
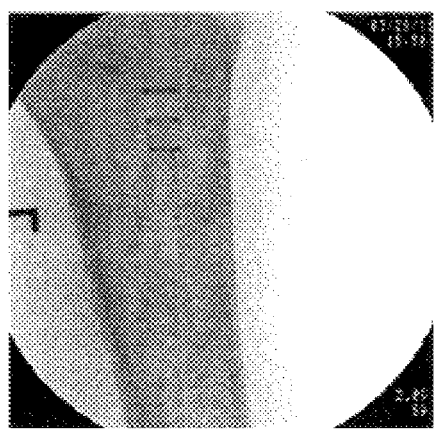

In one embodiment, the electrode was implanted on the tibial nerve, as shown in FIG. 3A. Proper implantation was verified by fluoroscopy visualization, as shown in FIG. 3B.

In one of five patients experiencing pain post lower-limb amputation, the extent of baseline pain intensity and relief of this pain by a self-administered narcotic pill were compared to the extent of each of baseline pain intensity and relief of this pain using the disclosed nerve block apparatus and method was self-assessed over a 21 consecutive day period. The patient self-assessed pain intensity using a 0-10 scale where 0 is no pain and 10 is as bad as it could be. The narcotic was hydrocodone/APAP formulated as a tablet at a dose of 10 mg/325 mg. The patient self-administered the tablet orally as needed.

When self-administering the electrical nerve block therapy, the parameters over which the patient did not have control were the amount of current applied, and the duration of each administration period. The parameters over which the patient did have control were the time(s) during the 24 hour period to self-administer the therapy, and the time interval between the administrations. In one embodiment, each treatment was for 10 minutes. In one embodiment, one self-administered electrical treatment for 10 minutes was immediately followed by at least one additional self-administered electrical treatment for 10 minutes to result in cumulative pain reduction effect. The amount of current/voltage applied during each interval ranged from 4 mApp to 26 mApp/4 Vpp to 20 Vpp, respectively.

Figure 5:
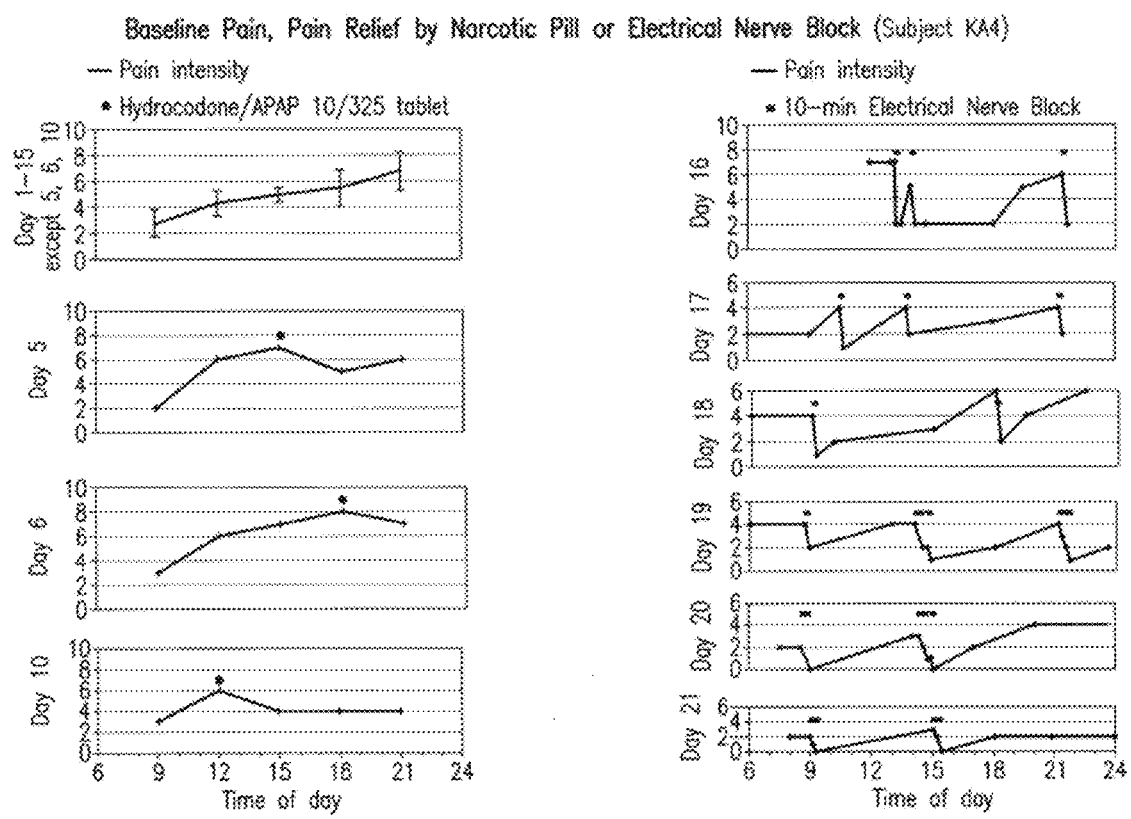
FIG. 5 graphs one patient's pain relief comparing use of the invention versus drug treatment.
Figure 6:
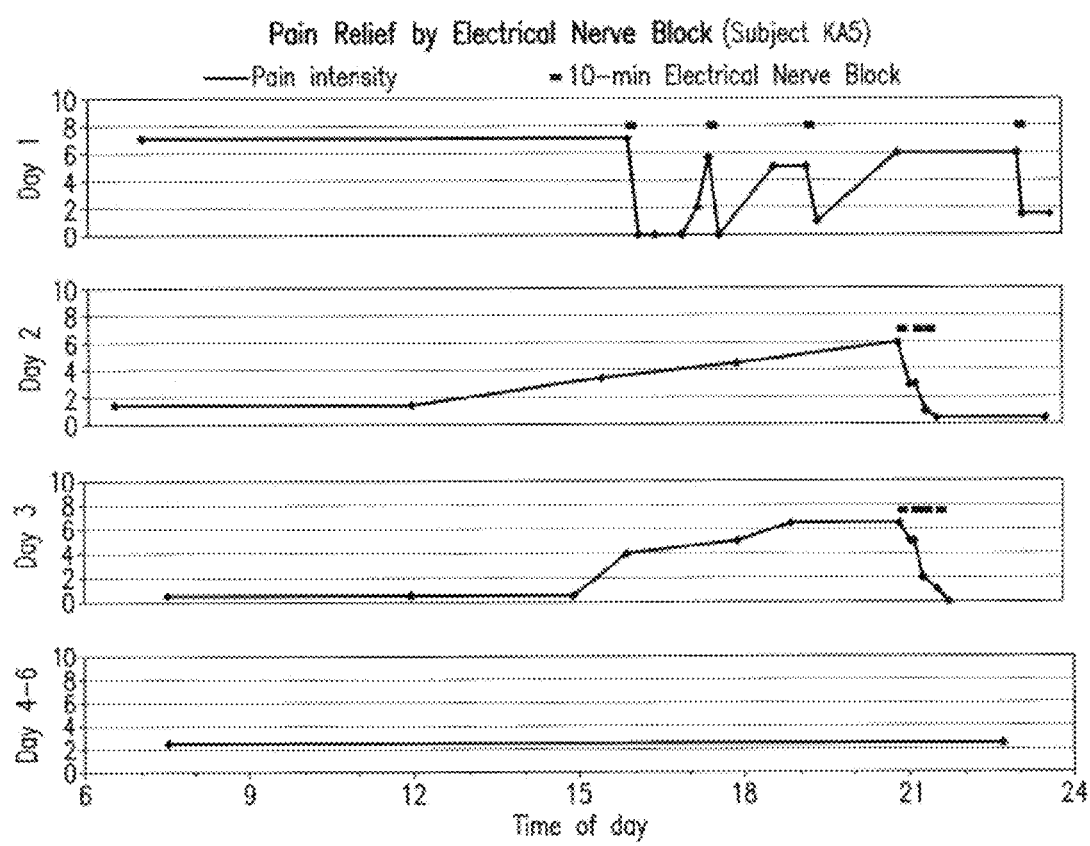
FIG. 6 graphs one patient's pain intensity and pain relief using the invention.

Specific selected data for each of two patients are shown in FIGS. 5 and 6 respectively. A summary of the results for all of the five patients is shown in FIG. 8.

The patients reported that they experienced pain mitigation within minutes of treatment onset. The patients reported that sensations such numbness, tingling, and pulling, subsided within minutes after treatment onset. The patients reported that, after a 10 min treatment (application of electrical blocking current), they experienced pain reduction that was sustained up to several hours after cessation of treatment.

A description of various embodiments of the electrode used for nerve conduction block is as follows. They differ from the use of the apparatus disclosed in Naples U.S. Pat. No. 4,602,624. Naples' electrode is used to stimulate, i.e., excite, activate, generate, an action potential in a nerve having a diameter of about 1 mm to about 3 mm. In Naples, four sets of rectangular-shaped electrodes constitute the contact points that are sandwiched between two layers of a non-conductive material such as silicon. The layers of non-conductive material were self-curling. The conductive contact points were disposed at uniform intervals therebetween at sites on the inner circumference of a first resiliently extensible layer. The conductive contact points are connected by conductive wires or leads, e.g., stainless steel wires. The layers have openings (windows) in the non-conductive material to expose the conductive contact points to the nerve upon selective regulation, in this case, activation to initiate an action potential. The distance between the openings (separation distance) and curling length of the layers is proportional to the nerve diameter.

In attempting to block an action potential in nerves having a diameter exceeding about 3 mm, the previously described apparatus and method is inadequate. This is because a simple scale-up of the aforementioned design did not permit adequate current flow that is necessary to block conduction of an action potential in a nerve that has a relatively larger diameter as compared to a typical nerve which has a diameter that does not exceed about 3 mm. For example, the sciatic nerve in an adult human has a diameter exceeding about 3 mm; it can be up to 12 mm diameter. The sciatic nerve is a frequent source of pathology and often requires therapy. The inventive method was used on nerves having a diameter exceeding about 3 mm for nerve conduction block.

In one embodiment the inventive method was used on nerves having a diameter between about 1 mm and about 8 mm. In one embodiment the inventive method was used on nerves having a diameter between about 3 mm and about 10 mm. In one embodiment the inventive method was used on nerves having a diameter between about 8 mm and about 12 mm. In one embodiment the inventive method was used on nerves having a diameter up to about 12 mm. The inventive method blocked an action potential in a nerve, including the sciatic nerve, and thus ameliorated and/or mitigated peripheral nerve pain. The inventive method was not used to generate an action potential in a nerve; rather, it was used to block conduction of an action potential. Blocking conduction of an action potential in a nerve, versus stimulating an action potential in a nerve, requires higher current, and hence lower resistance, at the interface between the nerve and the electrode. The inventive method used a generator that advantageously provided adequate voltage with lower power consumption. The inventive method thus minimized thermal damage to tissue from heat that was generated during its use, while providing improved efficiency.

In all embodiments, the electrode had a relatively larger contact surface with the nerve than conventional electrodes, such as Naples' electrode. As only one illustrative example used in the inventive method, the apertures were spaced at an interval ranging from 0.5 mm up to 1.9 mm. In one embodiment, the apertures were spaced at 1.0 mm intervals, defined as a center-to-center dimension between neighboring apertures.

Figure 4:
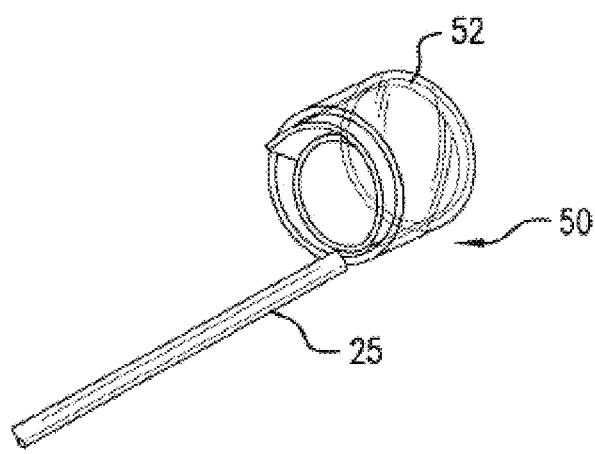
FIG. 4 schematically shows the nerve cuff electrode and lead.
Figure 7A:
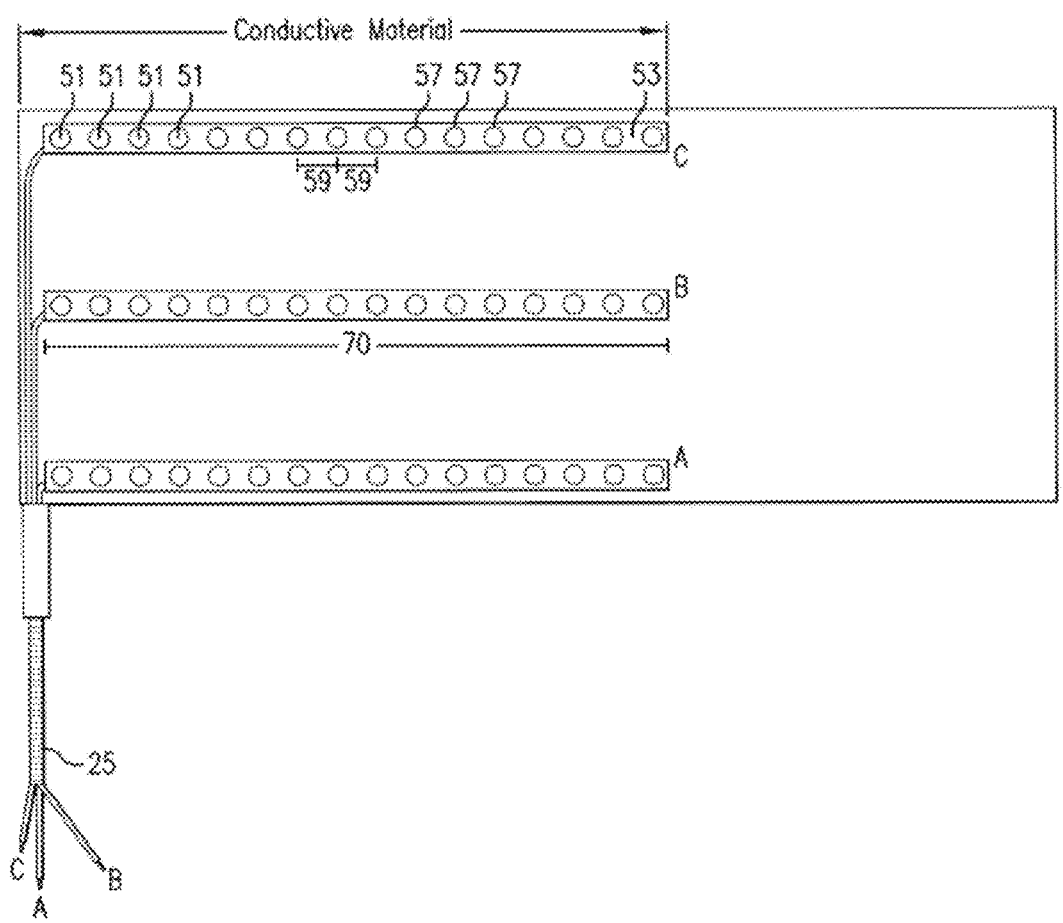
FIG. 7A shows a general schematic of a tripolar electrode in an uncurled configuration.
Figure 7B:
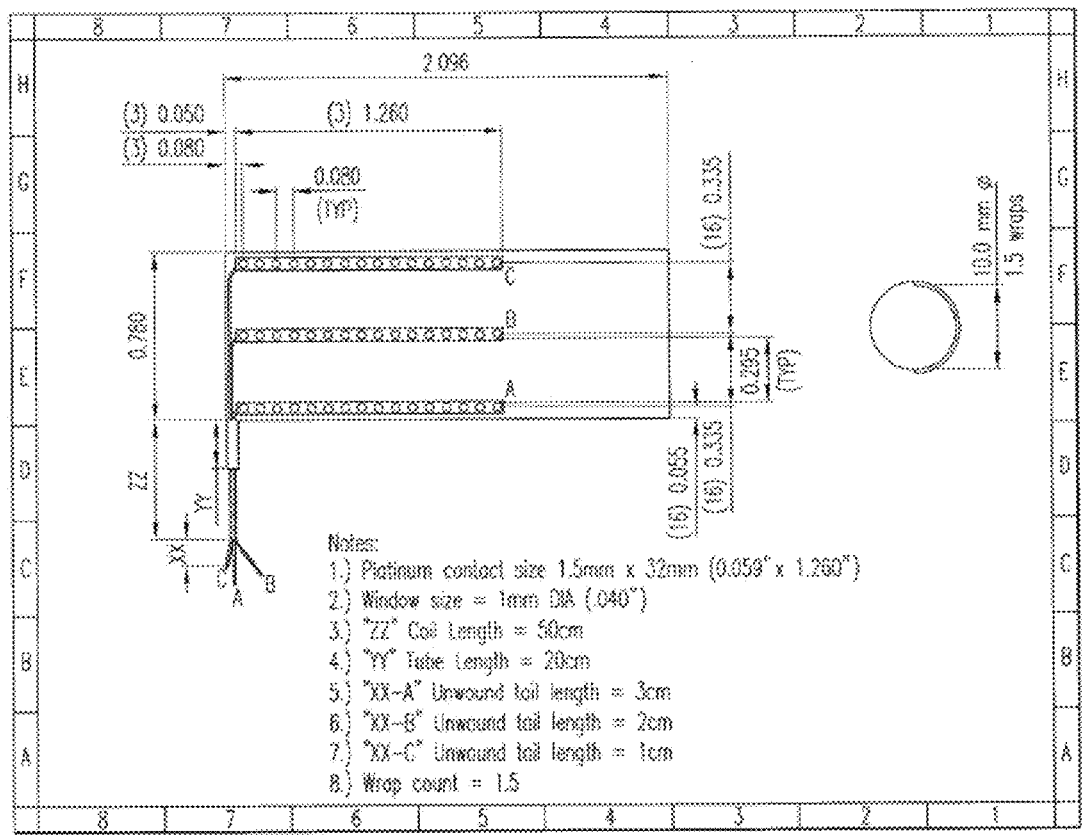
FIG. 7B shows one embodiment of FIG. 7A with specific dimensions.

As shown in FIG. 1, an external waveform generator 10 had an electrode connector 20 operatively connected with cable 25, having connector 13, LED indicator 15, and on/off indicator 17. As shown in use in FIGS. 2, 3, and 4, nerve cuff electrode 50 had conductive material 51 contained in self-curing sheet 53 and lead 25 to connect to the waveform generator 10. As best shown in FIGS. 7A, 7B, the conductive material 51 was both contained and retained within an implantable expandable spiral cuff 52, shown in FIG. 4. The cuff 52 provided the flexibility required for use to contact and regulate nerves having a diameter exceeding about 3 mm and up to about 12 mm, and provided a non-rigid contact surface with the nerve in order to minimize tissue damage.

In one embodiment, shown in general FIG. 7A and in one specific embodiment shown in FIG. 7B, the electrode contained continuous strips of conductive material 51, specifically platinum in FIG. 7B, in a sandwich configuration, with two opposing surfaces or sheets of a non-conductive material 53, specifically silicon in FIG. 7B, along the entire length of the non-conductive material 53. The non-conductive material 53 was self-curling. To provide points of contact of conductive material 51 with the nerve, around which the cuff 52 was implanted, openings or apertures 57 were created in one surface of the non-conductive material 53 at periodic intervals 59. The spacing of the intervals 59 is such that the conductive material 51 was contained and retained within the non-conductive material 53 during use, i.e., the non-conductive material does not pop out or come out, and provides sufficient exposure of the conductive material 51 for electrical contact with the nerve. In one embodiment, the openings 57 were created at 1 mm intervals. In one embodiment, the openings 57 were created at intervals ranging between about 1 mm to about less than 2 mm. The openings 57 were created in the non-conductive material 53; it was at these openings 57 that the nerve was exposed to the conductive material 51 in order to block conduction of an action potential. In a bi- or tri-polar embodiments, the distance or spacing between strips is 1:1 depending upon the nerve size to be treated; larger sized nerves can accommodate larger space between the strips. In FIG. 7A, for each electrode, the strip length with conductive material contacts 70 is shown for each of leads or wires A, B, and C. This electrode design achieved efficient current delivery to effect this blockage of the action potential. This electrode design contained and retained the conductive material 51 within the two layers of non-conductive material 53.

In one embodiment, the curled configuration of the apparatus had a diameter of 10 mm with a 1.5 wrap, meaning that one half of the circumference contained a single sandwiched sheet (i.e., 2 layers) of non-conductive material 53, and the other 1.5 wrap of the circumference contained two sandwiched sheets (i.e., 4 layers) of non-conductive material 53. Any wrap resulting in a compliant, flexible cuff that does not damage the nerve may be used. The interpolar distance was about 0.75 times to 1.5 times the inner cuff diameter. The contact surface area was relatively larger than the contact surface area of conventional electrodes, such as the electrode Naples disclosed for nerve stimulation and activation, safely delivered the required higher amount of charge to block the nerve action potential, even in nerves up to 12 mm in diameter.

In one embodiment, the electrode was bipolar. In another embodiment, the electrode used three contact groups, i.e., tripolar. In this embodiment, the electrode contained three continuous strips of conductive material, connected by electrically conductive leads (A, B, C in FIGS. 7A, 7B), that was provided between the two opposing non-conductive surfaces in the same manner as described above for two continuous strips of conductive material. The separation, i.e., distance, between the two, three, or more conductor bands is a function of the diameter of the cuff. The ratio of separation:diameter ranged between 0.75:1.5.

The above-described electrode blocked numerous nerve fascicles and/or nerve fibers. The blockage was reversible; the cuff was implantable along any length of nerve at any site, and electrical parameters (current, voltage, duration, etc.) were selected by the operator. In one embodiment, the recipient of the implantable apparatus is the operator. In one embodiment, a health care professional is the operator. Use of the electrode results in lower resistance at the interface between the nerve and the electrode. Such multiple points of contact, and relatively large openings, enables the electrode to block at least one portion of the nerve trunk. In the embodiment with a tripolar configuration, the electrode can be used to first block at least one portion of the nerve trunk, and then stimulate the other portion to verify blockage.

The inventive method has use in a variety of pain and non-pain applications. One embodiment uses the method and electrode to block peripheral nerve pain. Besides use to ameliorate amputation pain, the uses and description of which was previously described, other examples of ameliorating pain include, but are not limited to, ameliorating neuropathic pain, nociceptive pain, chronic neurogenic pain, migraine pain, post-herpetic neuralgia, pelvic pain, chronic post-surgical pain, post-surgical pain, and neuralgia. As known in the art, pain is defined as an unpleasant sensation caused by noxious stimulation of the sensory nerve endings. Amputation pain is pain resulting from the surgical removal of a part of the body or a limb or a part of a limb to treat for therapy resulting from, e.g., pathology, trauma, etc. Neuropathic pain is pain that results from the direct inputs of nervous tissue of the peripheral or central nervous system, generally felt as burning or tingling and often occurring in an area of sensory loss. Nociceptive pain is pain that results from stimulation of the neural receptors for painful stimuli, i.e., inputs of nociceptors. Chronic neurogenic pain is pain that originates in the nervous system and persists over time (i.e., not acute but chronic). Migraine pain result in headaches and is related to dilation of extracranial blood vessels, the origin of which may be defined (e.g., consumption of certain foods, external stimuli) or may be unknown. Post-herpetic neuralgia is a form of neuralgia with intractable pain that develops at the site of a previous eruption of herpes zoster. Pelvic pain is pain that is centered in the pelvis region i.e. lower part of the trunk of the body. Chronic post-surgical pain is pain persisting for a long period of time beginning after treatment of disease or trauma by manipulative and operative methods. Post-surgical pain is pain beginning after treatment of disease or trauma by manipulative and operative methods. Neuralgia is pain, often severe and characterized as "stabbing", resulting from any number of nervous system pathologies or disorders.

In other embodiments, the inventive method is used in non-pain applications where blocking the action potential of a nerve provides the desired amelioration outcome. One example of such a non-pain use is in ameliorating obesity. As known in the art, obesity is an abnormal increase in the proportion of fat cells, mainly in the viscera and subcutaneous tissues. The inventive method may be used on the vagus nerve in this embodiment. Another example of such a non-pain use in ameliorating overactive bladder, which is a colloquial term for bladder storage function disorders or pathologies. The method and electrode can be used on the pelvic nerve to ameliorate the sudden urge to void that may be difficult to suppress and may lead to incontinence. Another example of such a non-pain use is in ameliorating spasticity of any motor nerve; spasticity results in excessive muscle contraction and can be due to any of several nervous system disorders. The following hypothetical examples illustrate these embodiments.

A patient with advanced type 2 diabetes is experiencing neuropathic pain in his feet as a result of loss of blood flow to his legs. Normal doses of pain-killing narcotics are either ineffective or cause undesirable side effects. After implantation of the electrode and placement of the cuff on the right sciatic nerve trunk at the popliteal fossa, the patient self-treats pain for 10 minutes at 10 mApp, experiencing immediate pain relief. The patient repeats the procedure on demand, as needed.

A migraine patient experiences severe headaches unresponsive to conventional treatment. After implantation of the electrode and placement of the cuff on the greater occipital nerve trunk, the patient self-treats pain for 10 minutes at 10 mApp, experiencing immediate pain relief. The patient repeats the procedure on demand, as needed.

A patient with shingles experiences postherpetic neuralgia, unresponsive to conventional treatment. After implantation of the electrode and placement of the cuff on the intercostal nerves, the patient self-treats pain for 10 minutes at 10 mApp, experiencing immediate pain relief. The patient repeats the procedure on demand, as needed.

A post-operative inguinal hernia repair patient experiences chronic pain. After implantation of the electrode and placement of the cuff on the ilioinguinal nerve, the patient self-treats pain for 10 minutes at 10 mApp, experiencing immediate pain relief. The patient repeats the procedure on demand, as needed.

A patient with overactive bladder syndrome undergoes a procedure for implantation of the electrode and placement of the cuff on the pelvic nerve. The patient self-treats at 10 mApp upon an urge to urinate, experiencing urge cessation.

A patient with muscle spasticity undergoes a procedure for implantation of the electrode and placement of the cuff on a motor nerve. The patient self-treats at 10 mApp when needed, ameliorating spasticity of the muscle to which the nerve innervates.

EXAMPLE

High-Frequency Electrical Nerve Block for Postamputation Pain

The analgesic effect of kilohertz alternating current applied to the severed nerves in amputees afflicted by intractable limb pain was assessed in ten lower-limb amputees with chronic and severe residual limb pain or phantom limb pain who attained significant pain reduction after local nerve block injection. A cuff electrode was wrapped around the sciatic or tibial nerve. An external and/or implanted waveform generator was used. Sinusoidal waveforms of 10 kHz and up to 10 V were applied for 30 min during each subject-initiated treatment session. The patients recorded pain intensities before and after each session in a diary. Among the seven subjects who received treatment, the average pain reduction was 75% at the three-month primary end point. These subjects were responders per predefined criterion of achieving ≥50% pain reduction in ≥50% of treatment sessions for the three-month end point. Pain medication use and interference of pain on functions was significantly reduced. Treatment efficacy was sustained through the follow-up period of up to 12 months. All devices functioned as intended except for dislodgement and loss of function for one electrode in one subject. No changes of residual motor and sensory function were observed. The efficacy and safety of kilohertz electrical nerve block for postamputation pain were verified.

Postamputation pain (PAP) is highly prevalent in amputees and remains an extremely challenging pain condition to treat (1). The prevalence of PAP is greater than 1 million in the United States, which includes thousands of veteran amputees (2-4). Untreated PAP causes potential addiction to narcotic medications, continuous disability, and deteriorating quality of life. Formation of a neuroma, a ball-like tumor that grows at the end of severed nerves as a form of unregulated nerve regeneration (1), is often a direct cause for chronic PAP. An increased accumulation of molecules enhancing the expression of sodium channels in these neuromas results in hyperexcitability and spontaneous discharges (5). This abnormal peripheral activity is thought to be a source of stump pain as well as phantom pain (6, 7).

Surgical treatment of peripheral neuromas has been widely practiced but often fails to achieve long-term pain relief due to neuroma regrowth, leading to exploration of augmented or alternative methods to inhibit neuromas at amputation sites (8, 9). These methods, however, are usually neither effective nor painless, and some may even enhance neuropathic pain (8). Treatment of neuromas remains a complicated problem, and surgical resection alone was associated with an unacceptable recurrence rate (9).

Neuromodulation techniques such as spinal cord stimulation (SCS) and peripheral nerve stimulation (PNS) have been used to treat PAP, some specifically targeting the amputee population (1). SCS had a 34% (36/107) combined success rate of in five studies, while PNS had a 33% (4/12) combined success rate in four studies. Efficacy of these techniques in PAP was less robust than that in other neuropathic pain states. Nonsurgical treatments, such as pharmacological nerve blocks, have been widely practiced for short-term pain relief. Injection of local anesthetics such as lidocaine provided temporary pain relief in many patients, but their short-lasting effect and potential risk of local and systemic toxicity have prevented their long-term use (10,11). There was thus a need for a nerve-blocking method that acts like lidocaine without the burden of repeated injections and risk of toxicity.

The possibility of blocking nerve conduction by electric current, instead of chemical agents, has been explored (12, 13), with recent evidence and technical details on conduction block using high-frequency alternating current (HFAC). These studies demonstrated that continuous application of alternating current within the 5-50 kHz frequency range could result in a reliable and reversible conduction block in motor, sensory, and autonomic nerves in animal models (14-16). Computer simulation revealed that this type of conduction block is caused by inactivation of sodium channels due to continuous membrane depolarization by HFAC (17) and produced a true conduction block in peripheral nerves.

A first-in-human study evaluated the feasibility of electrical nerve block in reducing chronic pain in a small group of subjects during a short treatment period (21). Medically intractable limb pain in amputees was selected as the first specific indication based on medical need and technical feasibility. The rationale was to use this "electrical lidocaine" to block the pain signal at a location just proximal to the neuroma in a peripheral nerve by an implanted electrode. Four of the five subjects tested attained pain relief during in-clinic testing; two subjects used the treatment at home for one to two weeks with significant pain reduction. No adverse device effects occurred (22).

The study confirmed the finding of the first-in-human study in a larger-size and longer-term study in the same patient population (23, 24), justifying a new modality for managing PAP.

Subjects were recruited from the investigating physician's own patient pool via chart review, from referrals by local physicians, and from amputee-community targeted advertisements and publications; all subjects provided informed consent prior to participation. The key inclusion criteria were: amputation of lower or upper limb, chronic pain from amputation for ≥6 months, pain refractory to conventional medical management, severe pain in an amputated limb (worst pain intensity ≥7 on 0-10 Numerical Rating Scale [NRS]), frequent occurrence of severe pain (≥2 episodes/week on average), and significant pain reduction (≥50% on NRS) after local anesthetic injection for temporary nerve block. The key exclusion criteria were: active implanted devices, debilitating pain other than pain in the amputated limb, psychological comorbid conditions, and inability to accurately and reliably report pain intensity and related information.

Screening involved up to four visits in a period of up to four weeks. The first screening visit assessed eligibility per the above inclusion and exclusion criteria. Candidates who passed an initial eligibility assessment proceeded to receive the injection tests and start a diary for recording pain intensity and related information. Injection tests injected a dose of 1 mL saline followed by up to two doses of 5-20 mL 1% lidocaine near the target nerve, i.e., the sciatic nerve for above-knee amputees or tibial and common peroneal nerves for below-knee amputees. Ultrasound imaging was used to guide the needle to the target nerve. A pain reduction of ≥50% on NRS was defined as a positive response to an injection. A negative response to saline followed by a positive response to lidocaine was required to pass this test. To further reduce the possibility of false positive or negative findings, the injection test was repeated up to two times on different days. In addition to passing the injection test, the pain intensity and frequency reported by the daily diary had to satisfy the inclusion criterion on pain intensity and frequency to pass the final eligibility.

The devices used are shown in FIGS. 11A-D developed by Neuros Medical, Inc. (Cleveland Ohio). FIG. 11A shows the nerve cuff electrode. FIG. 11B shows the external waveform generator. FIG. 11C shows an implantable waveform generator. FIG. 11D shows a controller for the implantable generator of FIG. 11C.

The cuff electrode was a "self-sizing" design to prevent compression on the nerve trunk while ensuring nerve contact (25), platinum contacts embedded in a silicone substrate, and a bipolar configuration having an interpolar distance close to the cuff inner diameter for effective conduction block (18). The long-term performance safety and stability for the electrode-lead system had been demonstrated in multiple human studies, in which the leads crossed multiple joints in both lower and upper extremities without breakage (26, 27).

Placement of the electrode on the previously severed nerve was conducted under general anesthesia. The target nerves were exposed proximal to the neuroma formation at the tip of the severed nerve. The cuff electrode was wrapped around the target nerve using two pairs of conventional forceps. The lead from each electrode was connected to an extension cable, which was tunneled subcutaneously to an exit site at the antero-lateral aspect of the thigh. An external waveform generator generated a voltage-regulated sinusoidal waveform in the frequency range of 5 kHz-30 kHz. An implantable rechargeable waveform generator replaced the external generator with similar output parameters; it was implanted in a subcutaneous pocket in the abdominal region just below the rib cage in most subjects. The external remote controller was provided for the user to initiate a treatment session as needed.

One to two weeks after implantation surgery during a physician office visit, high-frequency sinusoidal waveforms were applied to each of the target nerves to check the initial response. The voltage was gradually increased to reach the level that induced a transient sensation, such as tingling, but not overly strong to cause discomfort or pain. Once an appropriate treatment voltage was found for each nerve through this initial testing, the generator was programmed in most cases with a frequency of 10 kHz, an initial voltage depending on the sensation threshold, a ramp-up duration of 5 min, a plateau voltage (treatment voltage), and a plateau duration of 25 min. After setting these preliminary parameters, a complete trial session of 30 min was conducted in the clinic. Two identical sliding potentiometers with 10-cm excursion and labeled with a scale of 0-10 were used for each subject to report the intensity of limb pain, as well as sensation induced by the treatment. The electrical signals representing the intensities of pain and sensation were captured with a data acquisition system for display and analysis. Based on the findings from the trial session, the parameters could be modified for optimal experience regarding pain relief or accompanying sensation. A one hour post-treatment lockout period was imposed to prevent continuous home use of the treatment.

Subjects used the device based on the need for pain relief, similar to taking a dose of pain medication. When the subject needed pain relief, the subject turned on the generator to receive a 30-min treatment. All parameters for the treatment were preset in the device during the office visit and could not be changed by the subject. The treatment outcomes were captured in a pain diary, with subjects instructed to record pain intensities immediately before and after each treatment session, in addition to the regular entries on a fixed interval of every three hours during waking periods. Subjects were instructed about permission to take their rescue pain medication if the device treatment did not provide adequate pain relief, and were required to record both dose and time of medication use in the diary.

After starting home treatment, subjects returned to the clinic weekly, then monthly, for follow-up visits. Pain diaries were reviewed during each follow-up visit to assess the general status of pain symptoms, the use of study treatment and pain medication, and the effect of the treatment or medication. In addition, an electronic data log within the generator that captured the time for each treatment session was retrieved. This machine-generated data were used to validate the subject-reported diary data. Adjustments on the device treatment parameters were occasionally made based on treatment effects or treatment-induced sensation.

The primary variable measured was subject-reported pain intensity, measured by the 0-10 NRS. Additional variables measured included pain interference to the activities of daily living (ADL), which was assessed by the interference subscale of Brief Pain Inventory (BPI) (28, 29). Data on pain medication use were collected by diary to corroborate the findings from the other variables.

Each subject's response to the treatment was quantified by the percentage pain reduction after each 30-min treatment session. A positive response was predefined as a 50% reduction in pain intensity, which is used by many trials on electrical stimulation for pain relief, such as spinal cord stimulator for low back pain and occipital nerve stimulation for migraine headache (30-32). This 50% reduction threshold also is the benchmark for defining a "substantial improvement" as defined in the IMMPACT recommendations on interpreting the clinical importance of treatment outcomes in chronic pain clinical trials (33). A responder was predefined as a subject who responded in at least one half of the treatment sessions in the defined period, i.e., a subject who experienced ≥50% pain reduction in ≥50% of the treatment sessions during the first three months (primary end point). Examples for responder determination are: during the first three months, subject X had 84 successful sessions out of a total of 117 treatment sessions, i.e., a proportion of success of 84/117=72%≥50%, thus a responder; subject Y had 34 successful sessions out of a total of 72 treatment sessions, i.e., a proportion of success of 34/72=47%<50%, thus a nonresponder.

Among the 24 amputees who had initial phone contact with the study site, 15 made an office visit and went through the informed consent process. Among the 15 consented subjects, 14 passed the injection tests, while one subject failed due to <50% pain reduction after lidocaine injection around the sciatic nerve. A total of ten subjects were implanted with electrodes per the enrollment limit of the approved protocol. Among them, one subject did not proceed to treatment because of significant pain relief after implantation surgery and use of a better-fitting prosthetic leg; two subjects did not proceed to treatment because of failure to respond during in-clinic testing. Thus, seven out of the ten implanted subjects received treatment and reached a three-month primary end point, after which one subject withdrew from the study due to a tendon-release surgery for improving mobility. The remaining six subjects were followed up to 6-12 months before the external generators were replaced with implanted generators per a protocol amendment, which specified an additional follow-up period of three months.

FIG. 9 shows demographics and amputation and pain characteristics collected at baseline for all ten subjects who proceeded to device implantation. Four were male and six are female with an average age of 54 years. The causes of amputation were mainly trauma (N=5) and vascular disease (N=4). The average time since amputation was seven years. The levels of amputation were 6 below-knee and 4 above-knee. Half of the subjects routinely used a prosthetic leg. Regarding pain characteristics, stump pain was dominant in seven subjects, while phantom pain was dominant in three subjects; average worst, usual, and least pain intensities were 9.7, 6.1, and 3.2, respectively; the frequency of pain episodes ranged from five to seven per day, to two per week. Most subjects (eight out of ten) used opioids for managing PAP at baseline. The average pain reduction after local lidocaine injection was 73%. None of the subjects received other forms of neuromodulation prior to enrollment.

Device functionality and subject response to HFAC application were first checked in clinic one to two weeks after surgery. All implanted devices were intact upon functional testing. Subject 8, the most recent amputee in the group, arrived with no pain in the limb. He considered that both the surgical process and his new better-fitting prosthetic leg, which he had received but had not used until after surgery, contributed to the resolution of the original pain. As a result of this "spontaneous" pain resolution, no data was generated from this subject on the treatment effect of electrical nerve block. Subjects 2 and 6 had moderate-to-severe pain during the visit, but did not attain meaningful pain relief through in-clinic testing and consequently did not proceed to treatment. These three subjects were later explanted and withdrawn from the study. The remaining seven subjects showed initial response to the treatment during in-clinic testing and proceeded to treatment at home.

FIG. 10 shows treatment parameters assigned to each of the seven subjects who proceeded to treatment. Target nerve diameters ranged from a 6-mm tibial nerve to a 12-mm sciatic nerve. Correspondingly, the treatment voltage (plateau voltage) ranged from 2 V to 10 V for effective pain relief. Subject 3 required >10 V for effective pain relief at the default frequency of 10 kHz mainly due to the large size of the sciatic nerve. Upon further testing, only 5.5 V was required at the alternative frequency of 5 kHz to achieve a similar effect on pain relief. The lower frequency was then adopted for treatment to reduce battery consumption. In addition to the plateau voltage, a default 5 min ramp-up duration was adopted and a nonzero initial voltage was sometimes set based on the sensation threshold in each subject to minimize the time that the subject did not feel initiation of the treatment. Subject 5 required a prolonged ramp duration to avoid discomfort related to preexisting, severe spasticity in the amputated leg.

Figure 12:
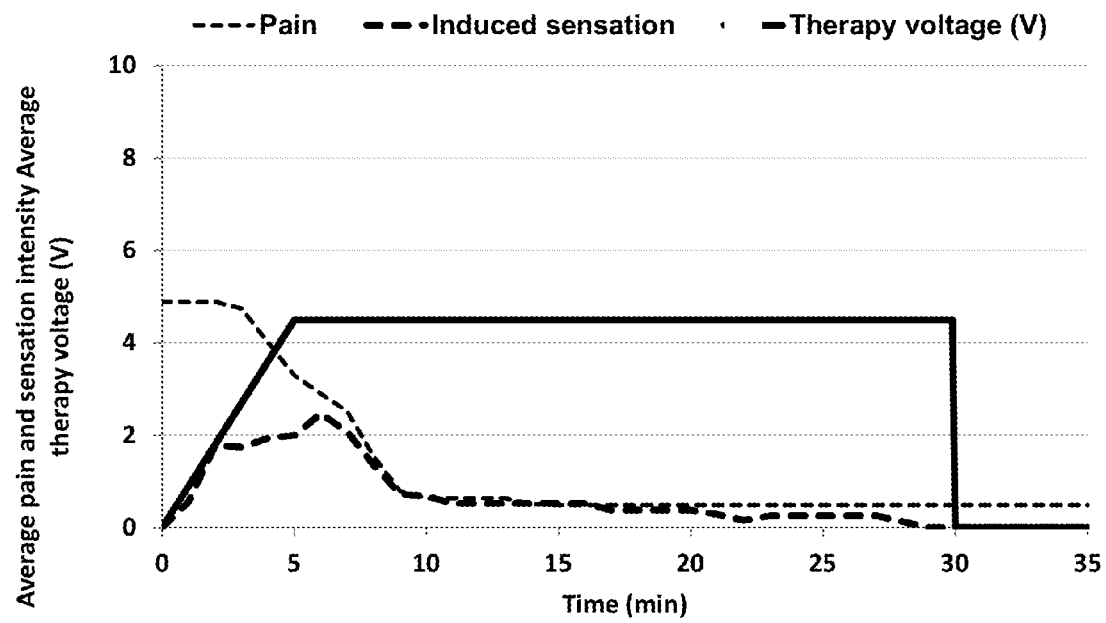
FIG. 12 graphs average pain intensity and therapy-induced sensation over a thirty minute therapy session for the patient group of FIG. 10.

FIG. 12 shows a representative profile of pain intensity and therapy-induced sensation during 30-min electrical nerve block therapy. It shows changing intensities of limb pain as well as HFAC-induced sensation. An additional trace shows the corresponding voltage contour applied through a treatment session. The plot reveals that the treatment-induced sensation, often tingling-like, increased during voltage ramp-up and subsided during voltage plateau, while pain intensity reduction occurred within minutes after treatment initiation and continued through the first 10 min of a treatment session on average.

The seven subjects initiated home treatment when pain presented by depressing the button on the external generator or the remote controller for the implanted generator. The subjects recorded the pain intensity immediately before and after each 30-min treatment session. The validity of each diary entry was checked against the electronic log in the generator during clinical visits, with 83% valid entries for the three-month primary phase, and 87% valid entries for the follow-up phase.

Figure 13A:
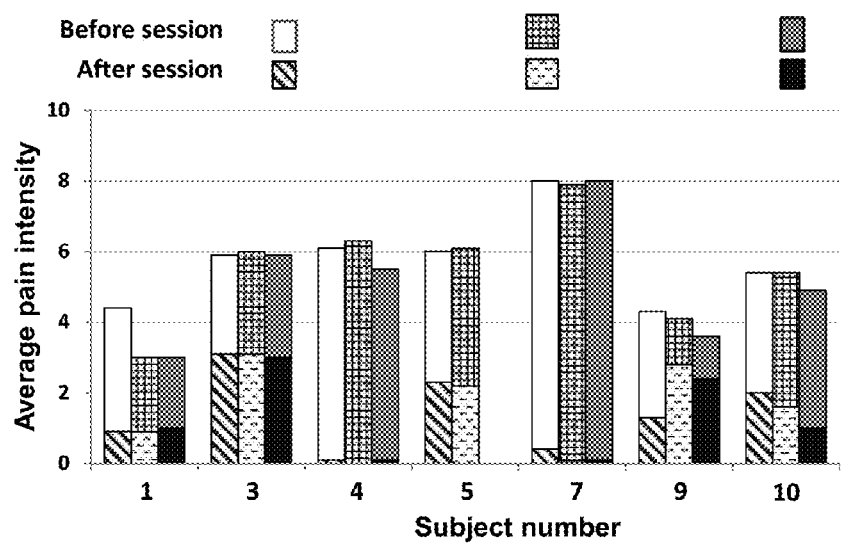
FIGS. 13A and 13B show pain reduction at three-month primary end point following therapy for the patient group of FIG. 10.
Figure 13B:
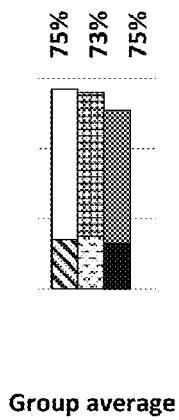
Figure 14A:
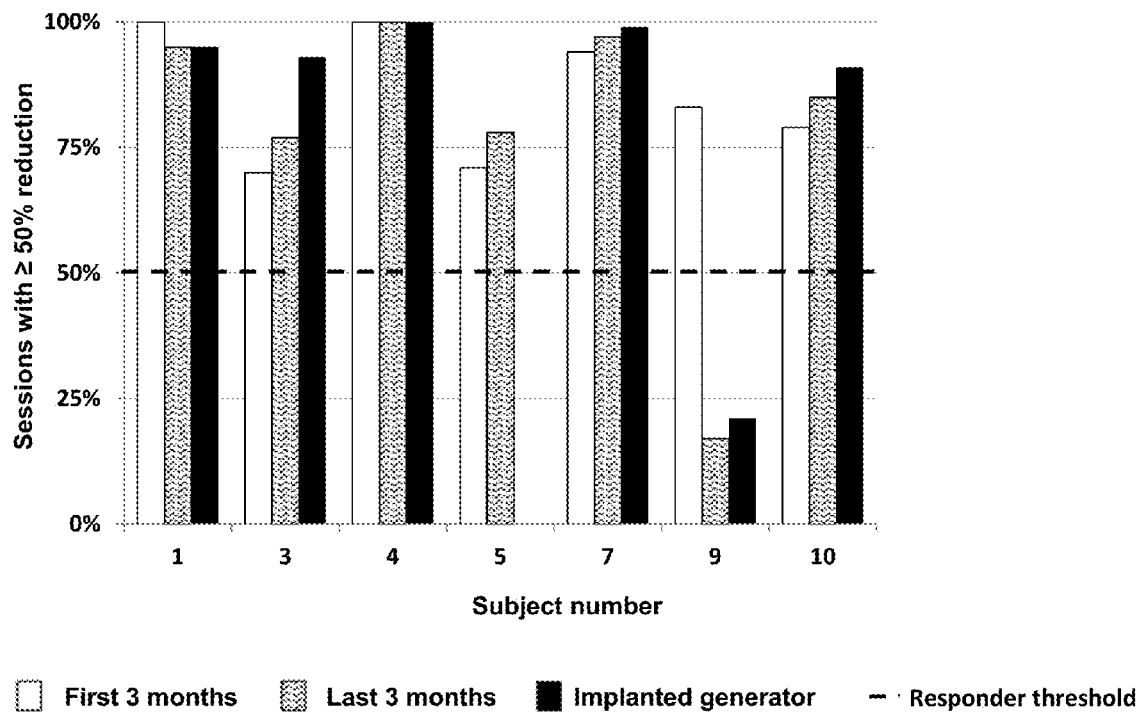
FIGS. 14A and 14B summarize therapy response rates at three-month primary end points and follow-up for the patient group of FIG. 10.
Figure 14B:
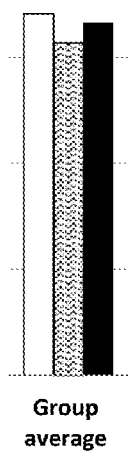

Pain reduction after each treatment session during the first three months, the primary outcome, was from 5.7 down to 1.4 (75% reduction) on average in the seven subjects based on data from 312 treatment sessions, as shown in FIGS. 13A and 13B. These subjects were responders by meeting the predefined criterion of attaining ≥50% pain reduction in more than one-half of the sessions, as shown in FIGS. 14A and 14B. Treatment efficacy was sustained through the initial follow-up period of up to 12 months (73% reduction) and the extended period of three months (75% reduction) after conversion to implanted generators in six of the seven responders. Subject 9, who was a responder during the first three months for primary end point, failed to meet the responder criterion of ≥50% pain reduction during the latter follow-up periods as the number of episodes of significant pain (NRS ≥5) reduced from 14 in the first three months down to one and zero in the two follow-up periods, respectively.

Figure 15A:
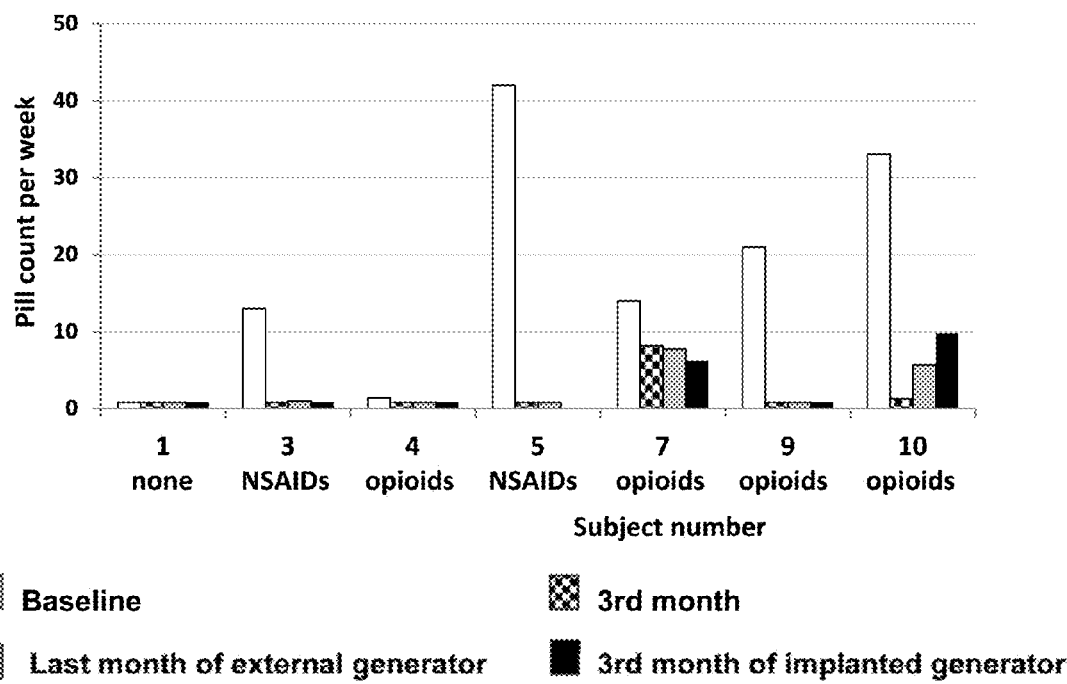
FIGS. 15A and 15B summarize reductions in medication usage for the patient group of FIG. 10.
Figure 15B:
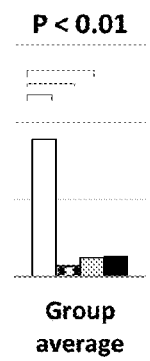

In addition to pain reduction immediately after each 30-min treatment session, pain relief often lasted for hours after a session; specifically, relief duration of around nine hours or greater was reported for 69% of the 276 sessions in which significant pain relief was attained. Besides pain reduction during and after treatment, pain medication use, one of the prespecified outcome variables, was significantly reduced, as shown in FIGS. 15A and 15B. This medication reduction occurred in subjects who took narcotic as well as those who only took non-narcotic pain medicines.

Figure 16A:
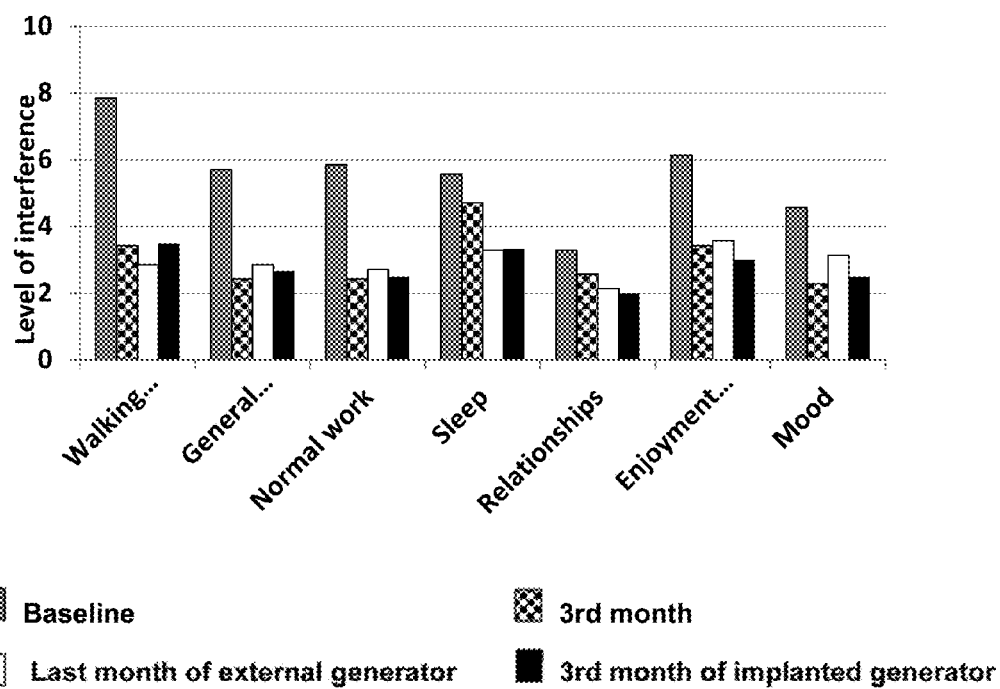
FIGS. 16A and 16B summarize pain interference reduction indicators for the patient group of FIG. 10.
Figure 16B:
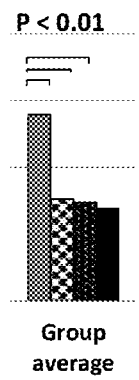

The impact of pain on function, measured by the pain interference score in the BPI (the other prespecified secondary outcome measure), also showed significant improvement. Results are shown in FIGS. 16A and 16B. All of the seven BPI categories showed improvement, with an average improvement of 46% at the third month and 50% at last follow-up. Walking ability (57%) and normal work (59%) were the most improved functions.

The nerve electrode in Subject 3 was dislodged during the first week after implantation and was replaced. The subject used the device during the following months with good outcome until week 26 when the electrode lost function again. The electrode was replaced during the surgery for conversion to the implantable generator. The electrode dislodgement and breakage were likely caused by excess mechanical stress resulting from sitting on the end of the stump, instead of the buttocks, due to an extremely short stump. This issue will be addressed by a more proximal implant location. The devices functioned as expected in the other six subjects. Residual motor and sensory function were unchanged during physical exams through the study period.

These results confirmed initial finding of the first-in-human study that chronic PAP was reduced by electrical nerve block in subjects who attained significant pain reduction after lidocaine block (23,24). The mechanism of action for this treatment is largely different from traditional neuromodulation techniques for pain management, such as PNS and SCS. The analgesic effect of this treatment was achieved by direct nerve conduction block by kilohertz frequency current, instead of indirect interaction with the central nervous system via "gate control" by low-frequency pulses (14,34). Such a direct conduction block may result in more effective, or at least more predictable, analgesia for pain with confirmed distal origin.

An important finding was that a brief application of 30 min of HFAC resulted in an extended period of pain relief lasting from tens of minutes to many hours after termination of electrical nerve block. This effect of electrical nerve block was consistent with pharmacological nerve block. In fact, pain relief duration far beyond the half-life of the injected analgesic agent was commonly observed in the injection screening process of this study as well as clinical practice (35). This extended pain relief duration could be the consequence of "winding down" or desensitization in both the peripheral and central nervous system during the temporary suppression of the afferent signals from the peripheral pain source. Besides the obvious clinical benefit, this extended pain relief also made the continuous delivery of HFAC unnecessary, a significant benefit for implementing an implantable battery-powered generator and reducing the burden of frequent recharging for the user.

The amputee population in this example included subjects with either stump pain or phantom pain alone, or both. Significant pain reduction was obtained in Subjects 3 and 9 with phantom pain in the toes and calf. In Subject 10, who suffered from both phantom and stump pain, the electrical nerve block was effective in reducing both types of pain, while pain medications prescribed were less effective in managing the phantom pain compared with stump pain. These results preliminarily evidenced that phantom limb pain could be caused or sustained by a peripheral pain source, consistent with recent reports (36, 37).

Improved screening will exclude recent amputees (<12 months since amputation surgery), who are likely still undergoing fitting for an optimal prosthetic, based on pain resolution in Subject 8. Criteria for passing injection screening will be more specific and stringent based on the finding that Subjects 2 and 6 did not respond to electrical nerve block after passing the injection tests. Upon review, it was found that both Subjects 2 and 6 passed screening only under uncommon conditions, compared with the standard conditions with all other subjects. Specifically, in Subject 2, 50% pain reduction was achieved only after extended duration of 30-40 min, instead of 20 min (only 25% and 38% reduction in the first 20 min after injections); in Subject 6, 50% pain reduction (from 8 to 4 in NRS) was achieved based on the elevated pain level after saline injection (8 in NRS), instead of pain level before saline injection (6 in NRS) as the baseline. Based on these findings, it is expected that an improved screening protocol with a clearly defined time period for assessing pain intensity after injection and a defined baseline for pain reduction calculation will improve the responder rate for this treatment. Retrospectively, the responder rate for this study would be 7 out of 7, instead of 7 out of 9, with the improved screening protocol.

The frequency used for this study was within the 4-40 kHz range suggested by animal study and computer simulation for effective conduction block (14, 17). These preclinical studies also showed that lower frequency in this range required lower amplitude to achieve conduction block, but induced a longer onset firing in the nerve prior to conduction failure. The 10 kHz default frequency for this study was a compromise between these two opposing factors. Only in Subject 3 was 5 kHz used for avoiding use of very high voltage of >10 V due to the large diameter of the target segment of the sciatic nerve.

For below-knee amputees, both tibial nerve and common peroneal nerve were attached with electrodes at a location just proximal to the popliteal fossa where the nerves were very close the surface. The reason for targeting both nerves instead of one was because the relative contribution to pain relief during injection block was unknown due to the proximity of the nerves and spread of injected agent. In general, the tibial nerve, which contains more sensory fibers to the distal part of the limb, provided more pain relief than the common peroneal during both in-clinic test and home use. Therefore, the electrode on the common peroneal was seldom activated due to minimal additional benefit.

The seven subjects who received treatment were responders as determined by the prespecified primary end point of attaining ≥50% pain reduction in ≥50% of the treatment sessions during the three-month treatment. These responses were sustained through the long-term follow-up of 6 to 12 months and beyond in most subjects. In addition to pain relief, pain medication use significantly decreased while functions improved; the most improved functions were walking ability and normal work, reflecting more prosthetic use due to less pain in the limb. This is an important outcome for function restoration in amputees (38-40). The safety of the device and the treatment were shown by the low failure rate of device and surgical procedure, as well as non-deterioration of residual motor or sensory functions.

In addition to PAP, electrical nerve block can ameliorate other neuropathic pains, such as various types of chronic postsurgical pain.

Electrical nerve block by HFAC applied on the peripheral nerve proximal to the neuroma reduced both residual-limb pain and phantom limb pain in amputees afflicted by chronic PAP. Pain relief was significant and sustainable. Pain medication use was significantly reduced, while daily functionality was significantly improved. No injuries or deterioration of residual function were observed.

1. Hsu and Cohen. Postamputation pain: epidemiology, mechanisms, and treatment. J Pain Res 2013; 6:121-136.
2. Ziegler-Graham et al. Estimating the prevalence of limb loss in the United States: 2005 to 2050. *Arch Phys Med Rehabil* 2008; 89:422-429.
3. Amputee Coalition of America. Amputation statistics by cause: limb loss in the United States. National limb loss information center fact sheet. http://www.amputee-coalitionsorg/fact_sheets/amp_stats_cause.pdf, Accessed Aug. 26, 2014, 2008.
4. Leland and Oboroceanu. American war and military operations and casualties:lists and statistics. CRS Report for Congress. Congressional Research Group. 1-27. http://fas.org/sgp/crs/natsec/RL32492.pdf, Accessed Aug. 26, 2014, 2010.
5. Dickinson et al. Maldynia: pathophysiology and management of neuropathic and maladaptive pain-a report of the AMA Council on Science and Public Health. Pain Med 2010; 11:1635-1653.
6. Flor et al. Phantom limb pain: a case of maladaptive CNS plasticity? Nat Rev Neurosci 2006; 7:873-881.
7. Subedi and Grossberg. Phantom limb pain: mechanisms and treatment approaches. Pain Res Treat 2011; 2011:864605.
8. Lewin-Kowalik. Prevention and management of painful neuroma. Neurol Med Chir (Tokyo) 2006; 46:62-68.
9. Guse and Moran. Outcomes of the surgical treatment of peripheral neuromas of the hand and forearm: a 25-year comparative outcome study. Ann Plast Surg 2013; 71:654-658.
10. Bouaziz and Benhamou. Neurologic complication of peripheral neural blockade. In Cousins et al. eds. Neural blockade in clinical anesthesia and pain medicine, 4th ed. Philadelphia.: Wolters Kluwer, Lippincott Williams and Wilkins, 2009:464-477.
11. Hadzit and Vloka. Neurologic complications of peripheral nerve blocks. In: Hadzit and Vloka, eds. Peripheral nerve blocks: principles and practice, 3rd ed. New York: The McGraw-Hill Company/New York School of Regional Anesthesia, 2004:67-77.
12. Kilgore and Bhadra. Nerve conduction block utilising high-frequency alternating current. Med Biol Eng Comput 2004; 42:394-406.
13. Kilgore and Bhadra. Reversible nerve conduction block using kilohertz frequency alternating current. Neuromodulation 2014; 17:242-255.
14. Bhadra N, Kilgore K L. High-frequency electrical conduction block of mammalian peripheral motor nerve. Muscle Nerve 2005; 32:782-790.
15. Lahowetz. Nerve conduction block in sensory nerves. M. S. Thesis. Case Western Reserve University, Cleveland, Ohio, 2007.
16. Waataja et al. Effects of high-frequency alternating current on axonal conduction through the vagus nerve. J Neural Eng 2011; 8:056013.
17. Bhadra et al. Simulation of high-frequency sinusoidal electrical block of mammalian myelinated axons. J Comput Neurosci 2007; 22:313-326.
18. Ackermann et al. Effect of bipolar cuff electrode design on block thresholds in high-frequency electrical neural conduction block. IEEE Trans Neural Syst Rehabil Eng 2009; 17:469-477.
19. Gerges et al. Frequency- and amplitude-transitioned waveforms mitigate the onset response in high-frequency nerve block. J Neural Eng 2010; 7:066003.
20. Ackermann et al. Electrical conduction block in large nerves: high-frequency current delivery in the nonhuman primate. Muscle Nerve 2011; 43:897-899.

21. Soin et al. Feasibility study on high-frequency electrical nerve block for amputation pain, Abstracts from the 10th World Congress of the International Neuromodulation Society; May 21-26, 2011; London, United Kingdom. Neuromodulation 2011; 14:561.
22. Soin et al. Short-term human testing of high-frequency nerve block for amputation pain. Presented at 15th Annual Meeting of North American Neuromodulation Society; December 8-11, Las Vegas, Nev., 2011.
23. Soin et al. Pilot study on high-frequency nerve block for amputation pain: initial results, Abstracts from the 11th World Congress of the International Neuromodulation Society; Jun. 8-13, 2013; Berlin, Germany. Neuromodulation 2013; 16: e98.
24. Soin et al. Pilot study on high-frequency nerve block for amputation pain: an update. Presented at 17th Annual Meeting of North American Neuromodulation Society; December 5-8, Las Vegas, Nev., 2013.
25. Naples et al. A spiral nerve cuff electrode for peripheral nerve stimulation. IEEE Trans Biomed Eng 1988; 35:905-916.
26. Polasek et al. Stimulation stability and selectivity of chronically implanted multicontact nerve cuff electrodes in the human upper extremity. IEEE Trans Neural Syst Rehabil Eng 2009; 17:428-437.
27. Fisher et al. Chronic stability and selectivity of four-contact spiral nerve-cuff electrodes in stimulating the human femoral nerve. J Neural Eng 2009; 6:046010.
28. Cleeland and Ryan. Pain assessment: global use of the Brief Pain Inventory. Ann Acad Med Singapore 1994; 23:129-138.
29. Keller et al. Validity of the brief pain inventory for use in documenting the outcomes of patients with noncancer pain. Clin J Pain 2004; 20:309-318.
30. Kumar et al. Spinal cord stimulation versus conventional medical management for neuropathic pain: a multicentre randomized controlled trial in patients with failed back surgery syndrome. Pain 2007; 132:179-188.
31. North et al. Spinal cord stimulation versus re-operation in patients with failed back surgery syndrome: an international multicenter randomized controlled trial (EVIDENCE study). Neuromodulation 2011; 14:330-336.
32. Saper et al. Occipital nerve stimulation for the treatment of intractable chronic migraine headache:ONSTIM feasibility study. Cephalalgia 2011; 31:271-285.
33. Dworkin et al. Interpreting the clinical importance of treatment outcomes in chronic pain clinical trials: IMMPACT recommendations. J Pain 2008; 9:105-121.
34. Melzack and Wall. Pain mechanisms: a new theory. Science 1965; 150:971-979.
35. Becker and Reed. Essentials of local anesthetic pharmacology. Anesth Prog 2006; 53:98-109.
36. Vaso et al. Peripheral nervous system origin of phantom limb pain. Pain 2014; 155:1384-1391.
37. Haroutounian et al. Primary afferent input critical for maintaining spontaneous pain in peripheral neuropathy. Pain 2014; 155:1272-1279.
38. Narang et al. Functional capabilities of lower limb amputees. Prosthet Orthot Int 1984; 8:43-51
39. Pohjolainen et al. Prosthetic use and functional and social outcome following major lower limb amputation. Prosthet Orthot Int 1990; 14:75-79.
40. Schoppen et al. Physical, mental, and social predictors of functional outcome in unilateral lower-limb amputees. Arch Phys Med Rehabil 2003; 84:803-811.

The embodiments shown and described are specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A method of relieving post-amputation pain in an amputee patient, the method comprising providing a device for administering a frequency between 5 kHz to 50 kHz to a nerve at a site proximal to a neuroma by a plurality of contact surfaces with the nerve to block conduction of an action potential in the nerve and not stimulate and not generate an action potential in the nerve, at a voltage between 4 V peak-to-peak (Vpp) to 20 Vpp or at a current between 4 mA peak-to-peak (mApp) to 26 mApp for an interval sufficient to relieve pain.

2. The method of claim 1 achieving at least equal analgesic effect in the patient in the absence of a pharmaceutical analgesic.

3. The method of claim 2 achieving at least one of enhanced analgesia efficacy or enhanced analgesia predictability compared to lidocaine block analgesia.

4. The method of claim 3 further comprising optionally repeating application of the waveform at an interval greater than lidocaine half-life.

5. The method of claim 4 where the neuropathic pain is selected from the group consisting of post-surgical pain, pain from shingles, neuropathic diabetic pain, migraine pain, and combinations thereof.

6. The method of claim 1 achieving at least equal analgesic effect in the patient relative to either spinal cord stimulation (SCS) and/or peripheral nerve stimulation (PNS).

7. The method of claim 1 further comprising optionally repeating application of the waveform at an interval not shorter than nine hours.

8. The method of claim 1 where the waveform generator is battery-powered and the interval decreases an interval for battery recharging.

9. The method of claim 1 where the waveform is applied by operatively connecting the nerve waveform generator to an implanted electrode.

10. The method of claim 1 where the waveform generator is implanted in the patient and is activated by a remote controller.

11. The method of claim 1 where the waveform generator is external to the patient and is activated at the waveform generator.

12. A method of relieving neuropathic pain in a patient in need thereof, the method comprising providing a device for administering a frequency between 5 kHz to 50 kHz to a nerve at a site proximal to a site of pain by a plurality of contact surfaces with the nerve to block conduction of an action potential in the nerve and not stimulate and not generate an action potential in the nerve, at a voltage between 4 V peak-to-peak (Vpp) to 20 Vpp or at a current between 4 mA peak-to-peak (mApp) to 26 mApp for an interval sufficient to relieve pain.

13. A method of providing improved mobility in an amputee above or below a knee, the method comprising providing a device for administering a frequency between 5 kHz to 50 kHz to a nerve at a site proximal to a neuroma by a plurality of contact surfaces with the nerve to block conduction of an action potential in the nerve and not stimulate and not generate an action potential in the nerve, at a voltage between 4 V peak-to-peak (Vpp) to 20 Vpp or at a current between 4 mA peak-to-peak (mApp) to 26 mApp for an interval sufficient to relieve pain facilitating tolerance of a lower limb prosthetic resulting in improved mobility.

14. The method of claim 13 where the nerve is selected from the group consisting of a tibial nerve or a sciatic nerve.

15. The method of claim 13 where the nerve diameter is up to 12 mm.

* * * * *

UNITED STATES PATENT AND TRADEMARK OFFICE
CERTIFICATE OF CORRECTION

| | | |
|---|---|---|
| PATENT NO. | : 9,295,841 B2 | Page 1 of 1 |
| APPLICATION NO. | : 14/656256 | |
| DATED | : March 29, 2016 | |
| INVENTOR(S) | : Zi-Ping Fang, Jon J. Snyder and Nemath Syed Shah | |

It is certified that error appears in the above-identified patent and that said Letters Patent is hereby corrected as shown below:

On Title Page, (73) Assignee:

"Meuros Medical, Inc." should read --Neuros Medical, Inc.--

Signed and Sealed this
Thirty-first Day of May, 2016

Michelle K. Lee
*Director of the United States Patent and Trademark Office*